US010597374B2

(12) United States Patent
Wiederhold et al.

(10) Patent No.: US 10,597,374 B2
(45) Date of Patent: Mar. 24, 2020

(54) INTEGRATED PROCESS FOR MAKING PROPENE AND PROPENE OXIDE FROM PROPANE

(71) Applicants: EVONIK DEGUSSA GMBH, Essen (DE); thyssenkrupp Industrial Solutions AG, Essen (DE)

(72) Inventors: Holger Wiederhold, Darmstadt (DE); David Bolz, Frankfurt (DE); Georg Friedrich Thiele, Friedberg (DE)

(73) Assignees: Evonik Operations GmbH, Essen (DE); thyssenkrupp Industrial Solutions AG, Essen (DE)

( * ) Notice: Subject to any disclaimer, the term of this patent is extended or adjusted under 35 U.S.C. 154(b) by 0 days.

(21) Appl. No.: 16/302,099

(22) PCT Filed: May 11, 2017

(86) PCT No.: PCT/EP2017/061355
§ 371 (c)(1),
(2) Date: Nov. 15, 2018

(87) PCT Pub. No.: WO2017/198546
PCT Pub. Date: Nov. 23, 2017

(65) Prior Publication Data
US 2019/0276419 A1 Sep. 12, 2019

(30) Foreign Application Priority Data
May 17, 2016 (EP) .................... 16169840

(51) Int. Cl.
*C07D 301/12* (2006.01)
*C07C 5/32* (2006.01)

(52) U.S. Cl.
CPC ............ *C07D 301/12* (2013.01); *C07C 5/324* (2013.01); *Y02P 20/125* (2015.11)

(58) Field of Classification Search
CPC .... C07D 301/12; C07D 303/04; C07C 5/324; Y02P 20/125
(Continued)

(56) References Cited
U.S. PATENT DOCUMENTS 4,308,409 A 12/1981 Wu et al.
5,274,140 A 12/1993 Venturello et al.
(Continued)

FOREIGN PATENT DOCUMENTS

DE 195 07 584 9/1996
EP 0 100 119 2/1984
(Continued)

OTHER PUBLICATIONS

International Search Report for PCT/EP2017/061355 filed May 11, 2017.
(Continued)

*Primary Examiner* — Taylor V Oh
(74) *Attorney, Agent, or Firm* — Law Office of: Michael A. Sanzo, LLC

(57) ABSTRACT

The integrated process comprises a step a) of dehydrogenating propane providing a stream S1 comprising propane and propene; a step b) of separating stream S1 in at least one rectification column, providing an overhead product stream S2 comprising more than 99% by weight propene, a side stream S3 comprising from 90 to 98% by weight propene and a bottoms product stream S4 enriched in propane; a step c) of reacting propene with hydrogen peroxide in the presence of an epoxidation catalyst using propene in molar excess; and a step d) of separating non-reacted propene and propene oxide from the reaction mixture of step c) providing a propene oxide product and a stream S5 comprising pro-
(Continued)

pene and propane; wherein stream S3 is passed to step c), stream S5 is recycled to step b) and stream S4 is recycled to step a).

17 Claims, 2 Drawing Sheets

(58) Field of Classification Search
USPC .......................................................... 549/518
See application file for complete search history.

(56) References Cited

U.S. PATENT DOCUMENTS

| | | | |
|---|---|---|---|
| 5,591,875 | A | 1/1997 | Chang et al. |
| 5,599,956 | A | 2/1997 | Pujado et al. |
| 6,372,924 | B2 | 4/2002 | Thiele |
| 6,673,950 | B1 | 1/2004 | Teles et al. |
| 6,861,042 | B2 | 3/2005 | Korl et al. |
| 7,169,945 | B2 | 1/2007 | Haas et al. |
| 7,173,143 | B2 | 2/2007 | Bender et al. |
| 7,601,263 | B2 | 10/2009 | Ebert et al. |
| 7,658,893 | B2 | 2/2010 | Bassler et al. |
| 7,670,572 | B2 | 3/2010 | Porscha et al. |
| 7,833,498 | B2 | 11/2010 | Goebbel et al. |
| 7,863,211 | B2 | 1/2011 | Strebelle et al. |
| 8,545,673 | B2 | 10/2013 | Dietz et al. |
| 9,539,549 | B2 | 1/2017 | Haensel et al. |
| 10,053,438 | B2 | 8/2018 | Bolz et al. |
| 10,053,440 | B2 | 8/2018 | Bolz et al. |
| 10,087,158 | B2 | 10/2018 | Stock et al. |
| 10,100,024 | B2 | 10/2018 | Stochniol et al. |
| 10,125,108 | B2 | 11/2018 | Jahn et al. |
| 10,214,471 | B2 | 2/2019 | Wiederhold et al. |
| 10,214,504 | B2 | 2/2019 | Brendel et al. |
| 10,399,952 | B2 | 9/2019 | Wöll |
| 10,428,035 | B2 | 10/2019 | Pascaly |
| 10,428,036 | B2 | 10/2019 | Hofen |
| 2003/0040637 | A1 | 2/2003 | Hofen et al. |
| 2005/0245751 | A1 | 11/2005 | Bender et al. |
| 2006/0014970 | A1 | 1/2006 | Goebbel et al. |
| 2006/0058539 | A1 | 3/2006 | Babler et al. |
| 2007/0004926 | A1 | 1/2007 | Schindler et al. |
| 2012/0142950 | A1 | 6/2012 | Teles et al. |
| 2015/0007951 | A1 | 1/2015 | Dietz et al. |
| 2017/0210718 | A1 | 7/2017 | Stochinol et al. |
| 2018/0002299 | A1 | 1/2018 | Bolz et al. |
| 2018/0002300 | A1 | 1/2018 | Bolz et al. |
| 2018/0030010 | A1 | 2/2018 | Breitenbach et al. |
| 2018/0030011 | A1 | 2/2018 | Stock et al. |
| 2018/0030012 | A1 | 2/2018 | Stock et al. |
| 2018/0057473 | A1 | 3/2018 | Stock et al. |
| 2018/0134676 | A1 | 5/2018 | Jahn et al. |
| 2018/0346432 | A1 | 12/2018 | Hofen et al. |
| 2018/0354878 | A1 | 12/2018 | Wiederhold et al. |
| 2018/0354923 | A1 | 12/2018 | Pascaly et al. |
| 2018/0370934 | A1 | 12/2018 | Brendel et al. |
| 2019/0023673 | A1 | 1/2019 | Schmidt |
| 2019/0100501 | A1 | 4/2019 | Wöll |

FOREIGN PATENT DOCUMENTS

| | | |
|---|---|---|
| EP | 0 230 949 | 8/1987 |
| EP | 0 659 473 | 6/1995 |
| EP | 0 757 045 | 2/1997 |
| EP | 1 247 806 | 10/2002 |
| EP | 1 489 074 | 12/2004 |
| WO | WO 02/085873 | 10/2002 |
| WO | WO 03/016296 | 2/2003 |
| WO | WO 03/018567 | 3/2003 |
| WO | WO 03/093255 | 11/2003 |
| WO | WO 2004/018088 | 3/2004 |
| WO | WO 2004/028962 | 4/2004 |
| WO | WO 2004/048335 | 6/2004 |
| WO | WO 2004/048354 | 6/2004 |
| WO | WO 2004/048355 | 6/2004 |
| WO | WO 2005/000827 | 1/2005 |
| WO | WO 2005/103024 | 11/2005 |
| WO | WO 2008/141734 | 11/2008 |
| WO | WO 2011/063937 | 6/2011 |
| WO | WO 2016/016070 | 2/2016 |

OTHER PUBLICATIONS

Written Opinion of the International Searching Authority for PCT/EP2017/061355 filed May 11, 2017.
International Preliminary Report on Patentability for PCT/EP2017/061355 filed May 11, 2017.
European Search Report for corresponding European application EP 16169840 filed May 17, 2016.
Chowdhury, et al, "Recovery of Homogeneous Polyoxometallate Catalysts from Aqueous and Organic Media by a Mesoporous Ceramic Membrane without Loss of Catalytic Activity," *Chem. Eur. J.* 12(11):3061-3066 (Apr. 2006).
Guojie, et al., "Factors Affecting Propylene Epoxidation Catalyzed by Reaction-Controlled Phase-Transfer Catalyst," *Chinese Journal of Catalysis* 26:1005-1010 (Nov. 2005), with English language abstract on p. 1 of the article.
Kaur, et al., "Poloxometalate-catalysed epoxidation of propylene with hydrogen peroxide: microemulsion versus biphasic process," *Catalysis Communications* 5(11): 709-713 (Nov. 2004).
Li, et al., "Influence of composition of heteropolyphosphatotungstate catalyst on epoxidation of propylene," *Journal of Molecular Catalysis A: Chemical* 218(2):247-252 (Aug. (2004).
Luthra, et al., "Homogeneous phase transfer catalyst recovery and re-use using solvent resistant membranes," *Journal of Membrane Science* 201:65-75 (2002).
Venturello, et al., "A New, Effective Catalytic System for Epoxidation of Olefins by Hydrogen Peroxide under Phase-Transfer Conditions," *J. Org. Chem.* 483831-3833 (1983).
Ullmanns Encyclopedia of Industrial Chemistry, online edition 2013, entry "propene," DOI 10.1002/14356007.a22_211.pub3.
U.S. Appl. No. 15/778,318, filed Nov. 1, 2016, US-2018/0370934 A1, Dec. 27, 2018, Brendel.
U.S. Appl. No. 15/778,337, filed May 23, 2018, US-2018/0354923 A1, Dec. 13, 2018, Pascaly.
U.S. Appl. No. 15/778,425, filed May 23, 2018, US-2018/0346432 A1, Dec. 6, 2018, Hofen.
U.S. Appl. No. 15/778,562, filed May 23, 2018, US-2018/0354878 A1, Dec. 13, 2018, Wiederhold.
U.S. Appl. No. 16/070,873, filed Jul. 18, 2018, Schmidt.
U.S. Appl. No. 16/086,309, filed Sep. 18, 2018, Wöll.

INTEGRATED PROCESS FOR MAKING PROPENE AND PROPENE OXIDE FROM PROPANE

CROSS REFERENCE TO RELATED APPLICATIONS

The present application is US national stage of international application PCT/EP2017/061355, which had an international filing date of May 11, 2017, and which was published on Nov. 23, 2017. Priority is claimed to European application EP 16169840.2, filed on May 17, 2016.

FIELD OF THE INVENTION

The present invention is directed to an integrated process for making propene and propene oxide from propane, which can be operated with varying product ratio.

BACKGROUND OF THE INVENTION

U.S. Pat. No. 5,599,956 describes an integrated process for the production of propene oxide, where propene is made from propane by dehydrogenation in a propene production unit and is reacted with hydrogen peroxide in an epoxidation zone to make propene oxide. Part of the propene produced may be diverted to other uses.

WO 2004/020423 describes an integrated method for synthesizing propene oxide which comprises dehydrogenating propane, separating hydrogen to obtain a stream T(2) containing propane and propene, separating stream T(2) into a stream T(5) having a high propane content and a stream T(3) having a high propene content and reacting stream T(3) with a stream containing hydrogen peroxide to obtain propene oxide. The document further discloses that a partial stream T(7) comprising propane and propene can be obtained in the step of reacting stream T(3) with hydrogen peroxide and that part or all of this stream may be returned to the step of separating stream T(2) if stream T(7) has a ratio of propane to propene of less than 1.

Ullmann's Encyclopedia of Industrial Chemistry, online edition 2013, entry "propene", DOI 10.1002/14356007.a22_211.pub3 describes the use of a double column process with a high pressure C3 splitter and a low pressure C3 splitter for separating propene and propane in FIG. 3. In this process, the reboiler of the low pressure C3 splitter is heated with overhead vapor from the high pressure C3 splitter and the overhead products from both columns are combined to provide a polymer grade propene.

SUMMARY OF THE INVENTION

It has now been found that in an integrated process for making propene oxide comprising a step of dehydrogenating propane to propene, the amount of equipment needed can be reduced by passing a propene stream recovered from a propene epoxidation to a rectification column separating the mixture of propene and propane obtained by dehydrogenating propane. It has also been found that such an integrated process can be operated more flexibly with different capacity utilization of the dehydrogenation and the epoxidation step when the rectification column is operated to provide two propene product streams with different contents of propane, using the propene product stream with the higher content of propane in the epoxidation step. Furthermore, it has been found that such a flexible operation with different capacity utilization can also be achieved for separating propene and propane with two thermally integrated rectification columns if the first of these columns is operated at a higher pressure, the propene product stream with the higher content of propane is withdrawn as a side stream from the first column and the propene stream recovered from the propene epoxidation is fed to the first column.

Subject of the invention is therefore an integrated process for making propene and propene oxide from propane comprising a) a step of dehydrogenating propane providing a stream S1 comprising propane and propene, wherein the combined amount of propane and propene in stream S1 is at least 95% by weight;

b) a step of separating stream S1 in at least one rectification column, providing an overhead product stream S2 comprising more than 99% by weight propene, a side stream S3 comprising from 90 to 98% by weight propene and a bottoms product stream S4 enriched in propane relative to stream S1;

c) a step of reacting propene with hydrogen peroxide in the presence of an epoxidation catalyst using propene in molar excess to hydrogen peroxide, providing a reaction mixture comprising propene oxide and non-reacted propene; and d) a step of separating non-reacted propene and propene oxide from the reaction mixture of step c) providing a propene oxide product and a stream S5 comprising propene and propane;

wherein stream S3 is passed to step c), stream S5 is recycled to the rectification column of step b) and stream S4 is recycled to step a).

In a preferred embodiment of this process, step b) is carried out in two thermally integrated rectification columns, where the first column is operated at a higher pressure than the second column, overhead vapor from the first column is used for heating the bottoms evaporator of the second column, streams S1 and S5 are fed to the first column, side stream S3 is withdrawn from the first column, the bottoms product of the first column is the feed to the second column, the bottoms product of the second column is withdrawn as stream S4 and the overhead products of the first and second column are combined to provide stream S2.

DETAILED DESCRIPTION OF THE INVENTION

Figure 1:
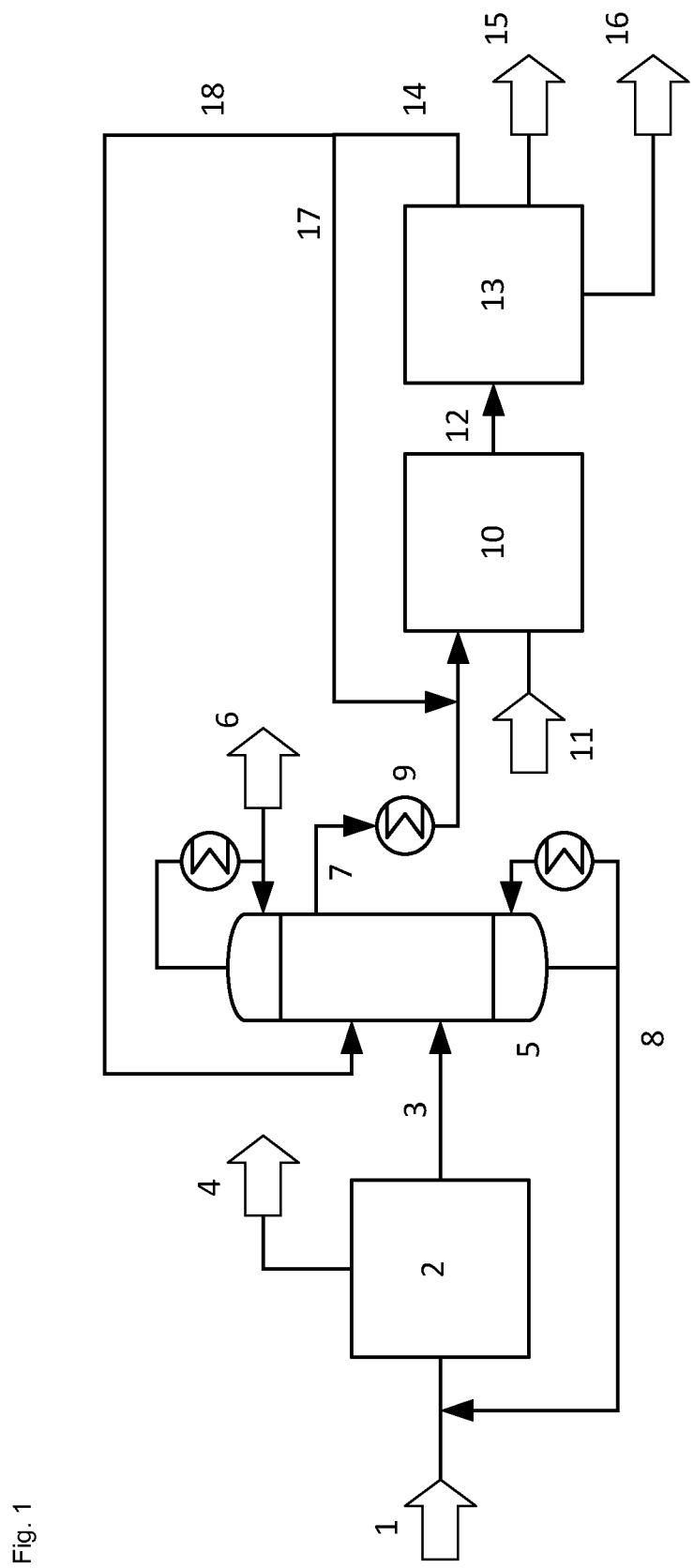
FIG. 1 shows an embodiment where a single rectification column is used for separating propene and propane.

The integrated process of the invention comprises a step a) of dehydrogenating propane, a separating step b) for separating a stream comprising propane and propene obtained in step a), a step c) of reacting propene with hydrogen peroxide in the presence of an epoxidation catalyst, and a step d) of separating non-reacted propene and propene oxide from the reaction mixture of step c).

In step a) of the integrated process of the invention, propane is dehydrogenated and a stream S1 is provided which comprises propane and propene with a combined amount of propane and propene of at least 95% by weight. Suitable methods for dehydrogenating propane are known from the prior art, for example from Ullmann's Encyclopedia of Industrial Chemistry, online edition 2013, entry "propene", chapter 3.3.1, DOI 10.1002/14356007.a22_211.pub3. Suitable methods for dehydrogenating propane are also available for license, for example the UOP Oleflex™ process from Honeywell UOP, the CATOFIN® process from CB&I Lummus, the STAR Process® by ThyssenKrupp Industrial Solutions or the PDH process from Linde and BASF. Stream S1 can be separated from the reaction mixture of the propane dehydrogenation reaction by separating hydrogen and hydrocarbons containing fewer than 3 carbon atoms through condensation and rectification using methods known from the prior art. In a preferred embodiment, a mixture of propane and hydrogen is passed through beds of a supported platinum catalyst in a series of moving bed reactors at a temperature of from 500 to 700° C. and a pressure of from 0.1 to 0.2 MPa. The resulting reaction mixture is cooled and compressed and a liquid mixture comprising propane and propene is separated by condensation. This liquid mixture is subjected to a selective partial hydrogenation using a palladium catalyst for converting propadiene and propyne to propene, followed by distillation in a de-ethanizer column, separating ethane and ethylene as an overhead product and providing stream S1 as a bottoms product.

In step b) of the integrated process of the invention, stream S1 is separated in at least one rectification column into an overhead product stream S2 comprising more than 99% by weight propene, a side stream S3 comprising from 90 to 98% by weight propene and a bottoms product stream S4 enriched in propane relative to stream S1. Stream S4 is recycled to step a) of dehydrogenating propane. The term side stream refers to a stream withdrawn from a rectification column at a withdrawal point between the column bottom and the column top, preferably from a withdrawal point that is at least 10 separation stages below the column top and at least 10 separation stages above the column bottom. The separation in step b) is preferably carried out to provide an overhead product stream S2 comprising from 99.5 to 99.8% by weight propene which can be used as polymer grade propene. Bottoms product stream S4 preferably comprises more than 90% by weight propane. The separation efficiency necessary to provide these compositions of streams S2, S3 and S4 can be achieved by adjusting the number of separation stages in the rectification column and the reflux ratio, a higher number of separation stages and a higher reflux ratio providing a better separation efficiency with a higher concentration of propene in stream S2 and a higher concentration of propane in stream S4. The one or more rectification columns used in step b) may comprise discrete trays, such as sieve trays or bubble cap trays, for providing the necessary number of separation stages. Alternatively, the rectification columns may contain one or more packings, which may be random packings or structured packings, structured packings being preferred. C3 splitter columns for separating propene and propane known from the prior art may be used for the integrated process of the invention if they are equipped with an additional conduit for withdrawing side stream S3. Side stream S3 may be withdrawn as a liquid stream or as a vapor stream. Preferably, side stream S3 is withdrawn as a vapor stream and condensed in a separate condenser after withdrawal. The one or more rectification columns are preferably operated at pressures of from 1.5 to 2.5 MPa in order to enable condensation of vapors with water cooling.

Step b) may be carried out in a single rectification column. The rectification column may have a simple side draw for withdrawing side stream S3 or may be a dividing wall column with the feed point for stream S1 and the side draw for withdrawing side stream S3 being separated by the dividing wall. The rectification column may be operated with vapor compression using the heat of condensation from the compressed vapor for heating the reboiler of the column. Step b) may also be carried out in two or more rectification columns which can be operated in series or in parallel.

In a preferred embodiment, step b) is carried out in two thermally integrated rectification columns. The first column is operated at a higher pressure than the second column and overhead vapor from the first column is used for heating the bottoms evaporator of the second column. Streams S1 and S5 are fed to the first column and side stream S3 is withdrawn from the first column. The bottoms product of the first column is the feed to the second column, the bottoms product of the second column is withdrawn as stream S4 and the overhead products of the first and second column are combined to provide stream S2. Side stream S3 is preferably withdrawn as a vapor stream and used for heating the bottoms evaporator of the second column. For this embodiment, the bottoms evaporator of the second column is equipped with at least two heat exchangers, one heated by the overhead vapor from the first column and one heated by vapor stream S3.

In step c) of the integrated process of the invention, propene is reacted with hydrogen peroxide in the presence of an epoxidation catalyst using propene in molar excess to hydrogen peroxide, providing a reaction mixture comprising propene oxide and non-reacted propene. Stream S3 is passed to this step to provide all or a part of the propene for the epoxidation reaction. The reaction is preferably carried out continuously.

Propene is used in excess to hydrogen peroxide, preferably with an initial molar ratio of propene to hydrogen peroxide of from 1.1:1 to 30:1, more preferably 2:1 to 10:1 and most preferably 3:1 to 5:1. Propene is preferably used in an excess sufficient to maintain an additional liquid phase rich in propene throughout step c). Using an excess of propene provides high reaction rate and hydrogen peroxide conversion and at the same time high selectivity for propene oxide.

Hydrogen peroxide can be used as an aqueous solution, preferably containing from 30 to 75% by weight hydrogen peroxide and most preferably from 40 to 70% by weight. Hydrogen peroxide from an anthraquinone process can be used, preferably a hydrogen peroxide having a composition as claimed in WO 2004/028962. Hydrogen obtained in step a) of dehydrogenating propane can be used in the anthraquinone process for making the hydrogen peroxide needed in step c).

The epoxidation catalyst can be a homogeneous catalyst or a heterogeneous catalyst. Suitable homogeneous epoxidation catalysts are manganese complexes with polydentate nitrogen ligands, in particular 1,4,7-trimethyl-1,4,7-triazacyclononane ligands, as known from WO 2011/063937. Other suitable homogeneous epoxidation catalysts are heteropolytungstates and heteropolymolybdates, in particular polytungstophosphates, as known from U.S. Pat. No. 5,274,140, preferably quaternary ammonium salts of a polytungstophosphate. Suitable heterogeneous epoxidation catalysts are titanium zeolites containing titanium atoms on silicon lattice positions. Preferably, a titanium silicalite catalyst is used, preferably with an MFI or MEL crystal structure. Most preferably a titanium silicalite 1 catalyst with MFI structure as known from EP 0 100 119 A1, is used. The titanium silicalite catalyst is preferably employed as a shaped catalyst in the form of granules, extrudates or shaped bodies. For the shaping process the catalyst may contain 1 to 99% of a binder or carrier material, all binders and carrier materials being suitable that do not react with hydrogen peroxide or with propene oxide under the reaction conditions employed for the epoxidation, silica being preferred as binder. Extrudates with a diameter of 1 to 5 mm are preferably used as fixed bed catalysts.

When the epoxidation catalyst is a titanium silicalite, the propene is preferably reacted with hydrogen peroxide in a methanol solvent to provide a liquid reaction mixture comprising methanol. The methanol solvent can be a technical grade methanol, a solvent stream recovered in the work-up of the epoxidation reaction mixture or a mixture of both. The epoxidation reaction is then preferably carried out at a temperature of 30 to 80° C., more preferably at 40 to 60° C., and at a pressure of from 1.9 to 5.0 MPa, more preferably 2.1 to 3.6 MPa and most preferably 2.4 to 2.8 MPa. The epoxidation reaction is preferably carried out with addition of ammonia to improve propene oxide selectivity as described in EP 0 230 949 A2. Ammonia is preferably added in an amount of from 100 to 3000 ppm based on the weight of hydrogen peroxide. The epoxidation is preferably carried out in a fixed bed reactor by passing a mixture comprising propene, hydrogen peroxide and methanol over a fixed bed comprising a shaped titanium silicalite catalyst. The fixed bed reactor is preferably equipped with cooling means and cooled with a liquid cooling medium. The temperature profile within this reactor is preferably controlled to maintain a maximum temperature within the catalyst bed of no more than 60° C., with the maximum temperature within the catalyst bed preferably being no more than 12° C. higher than the entry temperature of the cooling medium. The epoxidation reaction mixture is preferably passed through the catalyst bed in down flow mode, preferably with a superficial velocity of from 1 to 100 m/h, more preferably 5 to 50 m/h, most preferred 5 to 30 m/h. The superficial velocity is defined as the ratio of volume flow rate/cross section of the catalyst bed. Additionally it is preferred to pass the reaction mixture through the catalyst bed with a liquid hourly space velocity (LHSV) of from 1 to 20 h$^{-1}$, preferably 1.3 to 15 h$^{-1}$. It is particularly preferred to maintain the catalyst bed in a trickle bed state during the epoxidation reaction. Suitable conditions for maintaining the trickle bed state during the epoxidation reaction are disclosed in WO 02/085873 on page 8 line 23 to page 9 line 15. The methanol solvent is preferably used in the epoxidation in a weight ratio of 0.5 to 20 relative to the amount of aqueous hydrogen peroxide solution. The amount of catalyst employed may be varied within wide limits and is preferably chosen so that a hydrogen peroxide consumption of more than 90%, preferably more than 95%, is achieved within 1 minute to 5 hours under the employed epoxidation reaction conditions. Most preferably, the epoxidation reaction is carried out with a catalyst fixed bed maintained in a trickle bed state at a pressure close to the vapor pressure of propene at the reaction temperature, using an excess of propene that provides a reaction mixture comprising two liquid phases, a methanol rich phase and a propene rich liquid phase. Two or more fixed bed reactors may be operated in parallel or in series in order to be able to operate the epoxidation process continuously when regenerating the epoxidation catalyst. Regeneration of the epoxidation catalyst can be carried out by calcination, by treatment with a heated gas, preferably an oxygen containing gas, or by a solvent wash, preferably by the periodic regeneration described in WO 2005/000827.

In step d) of the integrated process of the invention, non-reacted propene and propene oxide are separated from the reaction mixture of step c), providing a propene oxide product and a stream S5 comprising propene and propane. Stream S5 is recycled to the rectification column of step b). In the preferred embodiment using two thermally integrated rectification columns in step b), stream S5 is preferably recycled to the first of the two rectification columns. Recycling stream S5 to the same rectification column from which stream S3 is withdrawn has the advantage that thermal integration of the columns can be maintained even when the fraction of propene withdrawn with stream S3 is varied.

The separation of non-reacted propene from the reaction mixture is preferably carried out to provide a recovered propene stream with a total content of propene and propane of more than 90% by weight, preferably at least 95% by weight. The separation of propene oxide and non-reacted propene can be carried out by methods known from the art, such as by distillation. Preferably, the reaction mixture is subjected to a pressure reduction and propene vapor formed by the pressure reduction is recompressed and cooled to provide the recovered propene stream by condensation. All or a part of the recovered propene stream can be recycled to step b) as stream S5.

When a solvent having a boiling point higher than propene oxide, such as methanol, is used in step c), the reaction mixture is preferably subjected to a pressure reduction, propene vapor formed by the pressure reduction is recompressed, and the compressed propene vapor is fed to a propene distillation column where it is separated to provide the recovered propene stream as the overhead product and a bottoms product containing compounds having a boiling point higher than propene and propane, such as propene oxide and the solvent. The bottoms product can be combined with the liquid mixture remaining after the pressure reduction.

When methanol is used as solvent, the liquid mixture remaining after the pressure reduction is preferably separated by distillation in a pre-separation column to provide an overhead product comprising propene oxide, methanol and residual propene and a bottoms product comprising methanol, water and non-reacted hydrogen peroxide. The pre-separation column is preferably operated to provide an overhead product comprising from 20 to 60% of the methanol contained in the liquid phase of the last pressure reduction step. The pre-separation column preferably has from 5 to 20 theoretical separation stages in the stripping section and less than 3 theoretical separation stages in a rectifying section and is most preferably operated without reflux and without a rectifying section to minimize the residence time of propene oxide in the pre-separation column. The pre-separation column is preferably operated at a pressure of from 0.16 to 0.3 MPa. Propene oxide and methanol are condensed from the overhead product of the pre-separation column and propene is preferably stripped from the resulting condensate in a propene stripping column which provides a bottom stream comprising propene oxide and methanol which is essentially free of propene. Propene oxide is preferably separated from the bottoms stream of the propene stripping column in an extractive distillation using water as the extraction solvent. The extractive distillation is preferably operated with additional feeding of a reactive compound containing an unsubstituted $NH_2$ group and capable of reacting with acetaldehyde during the extractive distillation, as described in WO 2004/048335. Extractive distillation with a reactive compound provides a high purity propene oxide containing less than 50 ppm of carbonyl compounds.

In a preferred embodiment, a part of the non-reacted propene separated in step d) as a recovered propene stream is combined with stream S3 to provide a propene feed to step c), which propene feed comprises from 24 to 20% by weight propane. The remainder of the non-reacted propene separated in step d) is recycled as stream S5 to step b).

Figure 2:
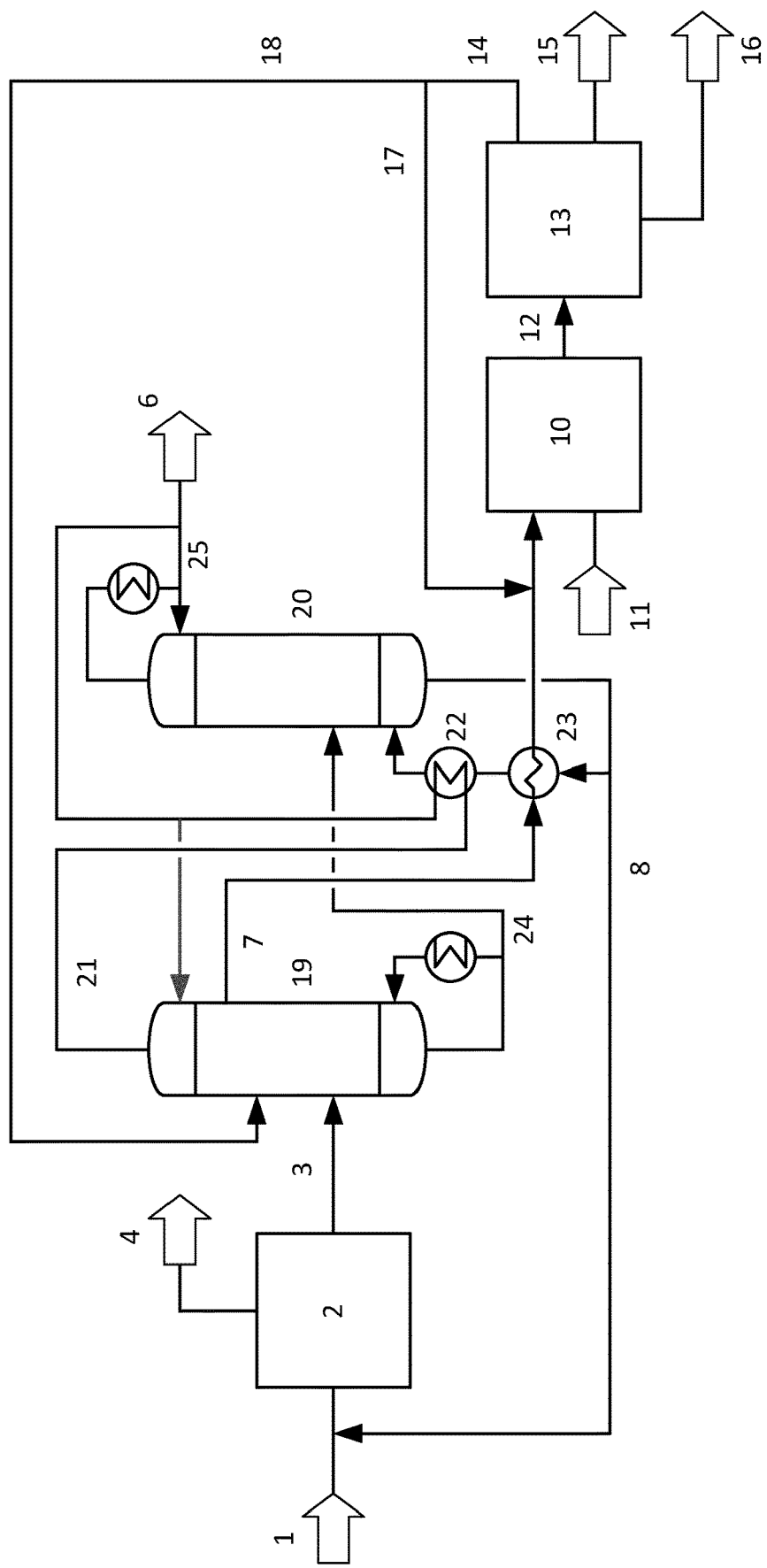
FIG. 2 shows an embodiment where two thermally integrated rectification columns are used for separating propene and propane.

FIGS. 1 and 2 show embodiments of the integrated process of the invention.

FIG. 1 shows an embodiment using a single rectification column in step b). Propane (1) is fed to a step a) (2) of dehydrogenating propane, providing a stream S1 (3) comprising propane and propene and a stream (4) comprising hydrogen formed by the dehydrogenation. Stream S1 (3) is fed to a rectification column (5) and an overhead product stream S2 (6), a side stream S3 (7) and a bottoms product stream S4 (8) enriched in propane are withdrawn from the rectification column (5). Stream S4 (8) is recycled to step a) (2). Side stream S3 (7) is withdrawn as a vapor stream, condensed in a condenser (9) and passed to a step c) (10) of reacting propene with hydrogen peroxide (11) in the presence of an epoxidation catalyst. The reaction mixture (12) comprising propene oxide product and non-reacted propene obtained in step c) (10) is passed to a step d) (13), where it is separated into a recovered propene stream (14), a propene oxide product (15) and a stream (16) comprising water and high boiling by-products. A part (17) of the recovered propene stream (14) is combined with stream S3 (7) to provide the propene feed to step c) (10) and the remainder of the recovered propene stream (14) is recycled to the rectification column (5) as stream S5 (18).

FIG. 2 shows an embodiment using two thermally integrated rectification columns (19, 20) in step b) and the same steps a), c) and d) as in FIG. 1. The first rectification column (19) is operated at a higher pressure than the second rectification column (20). Stream S1 (3) is fed to the first rectification column (19). The first rectification column (19) provides an overhead product stream (21), which is passed through a first heat exchanger (22) for heating the bottoms evaporator of the second rectification column (20). A side stream S3 (7) is withdrawn from the first rectification column (19), passed through a second heat exchanger (23) for heating the bottoms evaporator of the second rectification columns (20) and passed further to step c) (10) of reacting propene with hydrogen peroxide (11). The bottoms product (24) from the first rectification column (19) is fed to the second rectification columns (20). An overhead product stream (25) is withdrawn from the second rectification column (20), having a similar composition as the overhead product stream (21) from the first rectification column (19), and is combined with overhead product stream (21) to provide overhead product stream S2 (6). The bottoms product from the second rectification column (20) is withdrawn as stream S4 (8) and recycled to step a) (2).

The integrated process of the invention has further advantages when integrating a large scale propane dehydrogenation unit, providing economy of scale, with a smaller production unit for propene oxide, consuming only a part of the propene produced in the propane dehydrogenation. The integrated process provides polymer grade propene that can be used for producing polypropylene, but requires less energy than a process combining propane dehydrogenation and propene epoxidation where polymer grade propene is used in the epoxidation reaction. The preferred embodiment using two thermally integrated rectification columns provides more energy savings and can be operated with thermal integration of the two columns even when less or no propene is withdrawn as a side stream for the propene epoxidation.

LIST OF REFERENCE SIGNS

1 Propane
2 Step a) of dehydrogenating propane
3 Stream S1 comprising propane and propene
4 Stream comprising hydrogen
5 Rectification column
6 Overhead product stream S2
7 Side stream S3
8 Bottoms product stream S4 enriched in propane
9 Condenser
10 Step c) of reacting propene with hydrogen peroxide
11 Hydrogen peroxide
12 Reaction mixture
13 Step d) of separating non-reacted propene and propene oxide
14 Recovered propene stream
15 Propene oxide product
16 Stream comprising water and high boiling by-products
17 Part of the recovered propene stream
18 Stream S5 comprising propane and propene
19 First rectification column
20 Second rectification column
21 Overhead product stream from first rectification column
22 First heat exchanger
23 Second heat exchanger
24 Bottoms product from the first rectification column
25 Overhead product stream from second rectification column

EXAMPLES

The operation parameters of the rectification columns for separating stream S1 were calculated and optimized with the program Aspen Plus® of Aspen Technology, using set values for feed composition and compositions of withdrawn streams, pressure and number of separation stages and optimizing column diameter, reflux ratio, feed point locations and location of withdrawal point for side stream S3 for minimum reboiler energy consumption (reboiler duty).

Calculations were carried out for columns each having 175 separation stages, a feed stream S1 of 65.7 t/h containing 60% by weight propene and 40% by weight propane, a side stream S3 of 28.8 t/h containing 93% by weight propene and 7% by weight propane, a bottoms stream S4 containing 3.5% by weight propene and 96.5% by weight propane, an overhead product stream S2 containing 99.7% by weight propene and 0.3% by weight propane, a 25% conversion of propene in epoxidation step c) and a complete recycle of the recovered propene stream as stream S5. Calculation results are summarized in table 1.

In example 1, a single rectification column is used operating at 1.6 MPa with withdrawal of side stream S3 and use of side stream S3 as feed to epoxidation step c).

In comparative example 2, example 1 is repeated, but no side stream S3 is withdrawn and 26.8 t/h of overhead product stream S2 are used as feed to epoxidation step c).

In example 3, two rectification columns are used, the first operating at 2.17 MPa and the second operating at 1.6 MPa. Streams S1 and S5 are fed to the first rectification column, side stream S3 is withdrawn from the first rectification column, the bottoms product from the first rectification column is fed to the second rectification column, the bottoms product from the second rectification column is withdrawn as stream S4 and overhead product streams are withdrawn from both rectification columns with the target composition of stream S2.

In example 4, example 3 is repeated, but the first rectification column is operated at 1.6 MPa and the second rectification column is operated at 2.17 MPa.

In example 5, example 3 is repeated, but stream S5 is fed to the second rectification column.

In example 6, example 5 is repeated, but side stream S3 is withdrawn from the second rectification column.

In comparative example 7, example 3 is repeated, but no side stream S3 is withdrawn and 26.8 t/h of overhead product stream S2 are used as feed to epoxidation step c).

In comparative example 8, example 3 is repeated, but the second rectification column has 70 separation stages, no side stream S3 is withdrawn and the second column is operated to provide 28.8 t/h of an overhead product having the composition of stream S3 which is used as feed to epoxidation step c).

In comparative example 9, two rectification columns are used, the first operating at 1.6 MPa and having 175 separation stages and the second operating at 2.17 MPa and having 170 separation stages. Streams S1 and S5 are fed to the first rectification column, an overhead product having the composition of stream S3 is provided by the first rectification column, 28.8 t/h of this overhead product is used as feed to epoxidation step c) and the remainder is fed to the second rectification column, overhead product stream S2 is provided by the second rectification column, and bottom products having the composition of stream S4 are withdrawn from both rectification columns.

Example 1 and comparative example 2, as well as example 3 and comparative example 7 demonstrate that the integration of propane dehydrogenation and propene epoxidation using a common C3 splitter for separating propane and propene requires less energy and smaller equipment when a propene side stream with a higher propane content is withdrawn for the propene epoxidation, compared to a conventional operation of a C3 splitter and the use of the C3 splitter overhead product for the propene epoxidation.

Example 3 and comparative examples 4 to 8 demonstrate that the use of two thermally integrated columns with propene withdrawal for propene epoxidation as side stream and recycling of non-reacted propene from propene epoxidation both from and to the first column requires less energy and smaller equipment than other process configurations using two thermally integrated columns.

Two additional calculations were carried out for the column configuration of example 3, but without withdrawal of side stream S3 and without recycle stream S5. In the first calculation, stream S1 was kept constant, which lead to an increased flow rate of overhead product stream S2, and in the second calculation, stream S1 was reduced to provide the same flow rate of overhead product stream S2 as in example 3. In both cases, heat integration of the thermally integrated rectification columns could be maintained. Additional calculations with the tray dimensioning program SulCol of Sulzer confirmed that the separations of example 3 and of both these cases can be carried out with the same rectification columns without exceeding tray operation ranges. This demonstrates that the advantages of two thermally integrated columns can be achieved for different operating rates of the propane dehydrogenation and the propene epoxidation, even up to a complete shutdown of the propene epoxidation unit. The process of the invention using two thermally integrated columns therefore provides flexibility in the operating rates of propane dehydrogenation and propene epoxidation without compromising energy efficiency.

TABLE 1

| Example | 1 | 2 | 3 | 4 | 5 | 6 | 7 | 8 | 9 |
|---|---|---|---|---|---|---|---|---|---|
| First column | | | | | | | | | |
| Diameter in m | 9.41 | 9.82 | 6.88 | 6.21 | 7.66 | 7.38 | 7.18 | 6.98 | 7.44 |
| Feed point for stream S5* | 88 | 6 | 81 | 76 | | | 6 | 130 | 2 |
| Feed point for stream S1* | 139 | 136 | 160 | 159 | 134 | 159 | 172 | 170 | 102 |
| Withdrawal point of stream S3* | 68 | | 74 | 74 | 51 | | | | |
| Reflux ratio | 20.4 | 11.8 | 26.9 | 20.6 | 107.1 | 21.2 | 10.4 | 13.8 | 7.1 |
| Reboiler duty in MW | 60.4 | 63.8 | 33.3 | 34.2 | 38.4 | 36.6 | 35.3 | 40.2 | 43.5 |
| Second column | | | | | | | | | |
| Diameter in m | | | 5.98 | 7.23 | 6.67 | 6.45 | 6.24 | 8.16 | 8.29 |
| Feed point from first column | | | 137 | 135 | 161 | 141 | 137 | 70 | 111 |
| Feed point for stream S5* | | | | | 105 | 42 | | | |
| Withdrawal point of stream S3* | | | | | | 40 | | | |
| Reflux ratio | | | 21.0 | 30.8 | 15.3 | 38.0 | 20.5 | 17.7 | 17.5 |
| Reboiler duty in MW | | | 31.9 | 34.7 | 37.4 | 35.6 | 34.0 | 40.9 | 44.3 |

*Separation stages counted from column top

The invention claimed is:

1. An integrated process for making propene and propene oxide from propane, comprising:
   a) a step of dehydrogenating propane to provide a stream, S1, comprising propane and propene, wherein the combined amount of propane and propene in stream S1 is at least 95% by weight;
   b) a step of separating stream S1 in at least one rectification column to provide:
      i) an overhead product stream, S2, comprising more than 99% by weight propene;
      ii) a side stream, S3, comprising from 90 to 98% by weight propene; and
      iii) a bottoms product stream, S4, enriched in propane relative to stream S1;
   c) a step of reacting propene with hydrogen peroxide in the presence of an epoxidation catalyst using propene in molar excess to hydrogen peroxide, to provide a reaction mixture comprising propene oxide and non-reacted propene; and
   d) a step of separating non-reacted propene and propene oxide from the reaction mixture of step c) to provide a propene oxide product and a stream, S5, comprising propene and propane;
   wherein: stream S3 is passed to step c); stream S5 is recycled to the rectification column of step b); and stream S4 is recycled to step a).

2. The process of claim 1, wherein step b) is carried out in a single rectification column.

3. The process of claim 1, wherein:

step b) is carried out in two thermally integrated rectification columns, wherein the first column is operated at a higher pressure than the second column, and overhead vapor from the first column is used for heating the bottoms evaporator of the second column;

streams S1 and S5 are fed to the first column;

side stream S3 is withdrawn from the first column;

the bottoms product of the first column is the feed to the second column;

the bottoms product of the second column is withdrawn as stream S4; and the overhead products of the first and second column are combined to provide stream S2.

4. The process of claim 3, wherein side stream S3 is withdrawn as a vapor stream and used for heating the bottoms evaporator of the second column.

5. The process of claim 1, wherein stream S4 comprises more than 90% by weight propane.

6. The process of claim 3, wherein stream S4 comprises more than 90% by weight propane.

7. The process of claim 1, wherein a part of the non-reacted propene separated in step d) is combined with stream S3 to provide a propene feed to step c), said propene feed comprising from 2 to 20% by weight propane, and the remainder of the non-reacted propene separated in step d) is recycled as stream S5 to step b).

8. The process of claim 3, wherein a part of the non-reacted propene separated in step d) is combined with stream S3 to provide a propene feed to step c), said propene feed comprising from 2 to 20% by weight propane, and the remainder of the non-reacted propene separated in step d) is recycled as stream S5 to step b).

9. The process of claim 5, wherein a part of the non-reacted propene separated in step d) is combined with stream S3 to provide a propene feed to step c), said propene feed comprising from 2 to 20% by weight propane, and the remainder of the non-reacted propene separated in step d) is recycled as stream S5 to step b).

10. The process of claim 6, wherein a part of the non-reacted propene separated in step d) is combined with stream S3 to provide a propene feed to step c), said propene feed comprising from 2 to 20% by weight propane, and the remainder of the non-reacted propene separated in step d) is recycled as stream S5 to step b).

11. The process of claim 1, wherein, in step c), the initial molar ratio of propene to hydrogen peroxide is from 3:1 to 5:1.

12. The process of claim 3, wherein in step c) the initial molar ratio of propene to hydrogen peroxide is from 3:1 to 5:1.

13. The process of claim 5, wherein in step c) the initial molar ratio of propene to hydrogen peroxide is from 3:1 to 5:1.

14. The process of claim 7, wherein in step c) the initial molar ratio of propene to hydrogen peroxide is from 3:1 to 5:1.

15. The process of claim 8, wherein in step c) the initial molar ratio of propene to hydrogen peroxide is from 3:1 to 5:1.

16. The process of claim 9, wherein in step c) the initial molar ratio of propene to hydrogen peroxide is from 3:1 to 5:1.

17. The process of claim 10, wherein in step c) the initial molar ratio of propene to hydrogen peroxide is from 3:1 to 5:1.

\* \* \* \* \*